United States Patent [19]

Lakowicz et al.

[11] Patent Number: 5,246,867
[45] Date of Patent: Sep. 21, 1993

[54] DETERMINATION AND QUANTIFICATION OF SACCHARIDES BY LUMINESCENCE LIFETIMES AND ENERGY TRANSFER

[75] Inventors: Joseph R. Lakowicz, Columbia; Badri P. Maliwal, Baltimore, both of Md.; Peter A. Koen, Hillsborough, N.J.

[73] Assignees: University of Maryland at Baltimore, Md.; Becton Dickinson & Company, N.J.

[21] Appl. No.: 822,382

[22] Filed: Jan. 17, 1992

[51] Int. Cl.$^5$ ............... G01N 21/64; G01N 33/66
[52] U.S. Cl. ............... 436/95; 422/82.07; 422/82.08; 436/94; 436/172
[58] Field of Search ............... 436/94, 95, 172; 422/82.07, 82.08

[56] References Cited

U.S. PATENT DOCUMENTS

| | | | |
|---|---|---|---|
| 4,344,438 | 8/1982 | Schultz | 128/634 |
| 4,865,995 | 9/1989 | Dairaku | 436/178 X |
| 4,929,561 | 5/1990 | Hirschfeld | 436/116 |

Primary Examiner—Jill A. Johnston
Attorney, Agent, or Firm—Wegner, Cantor, Mueller & Player

[57] ABSTRACT

A method for measuring the concentration of a saccharide, conjugated saccharide or polysaccharide of interest using luminescent lifetimes and energy transfer in which an energy transfer donor-acceptor pair is added to a sample to be analyzed, the donor of the donor-acceptor pair being photoluminescent. The acceptor is bound to a carrier, while the donor and any saccharide, conjugated saccharide or polysaccharide of interest present in the sample compete for binding sites on the carrier. The sample is irradiated and the resultant emission detected. Energy transfer occurs between the donors and the acceptors, which produces a detectable lifetime change of the fluorescence of the donor. The lifetime change is reduced or even eliminated by the competitive binding of a saccharide, conjugated saccharide or polysaccharide of interest to the donor. By measuring the apparent luminescent lifetime, the amount of a saccharide, conjugated saccharide or polysaccharide of interest in the sample can be determined.

15 Claims, 23 Drawing Sheets

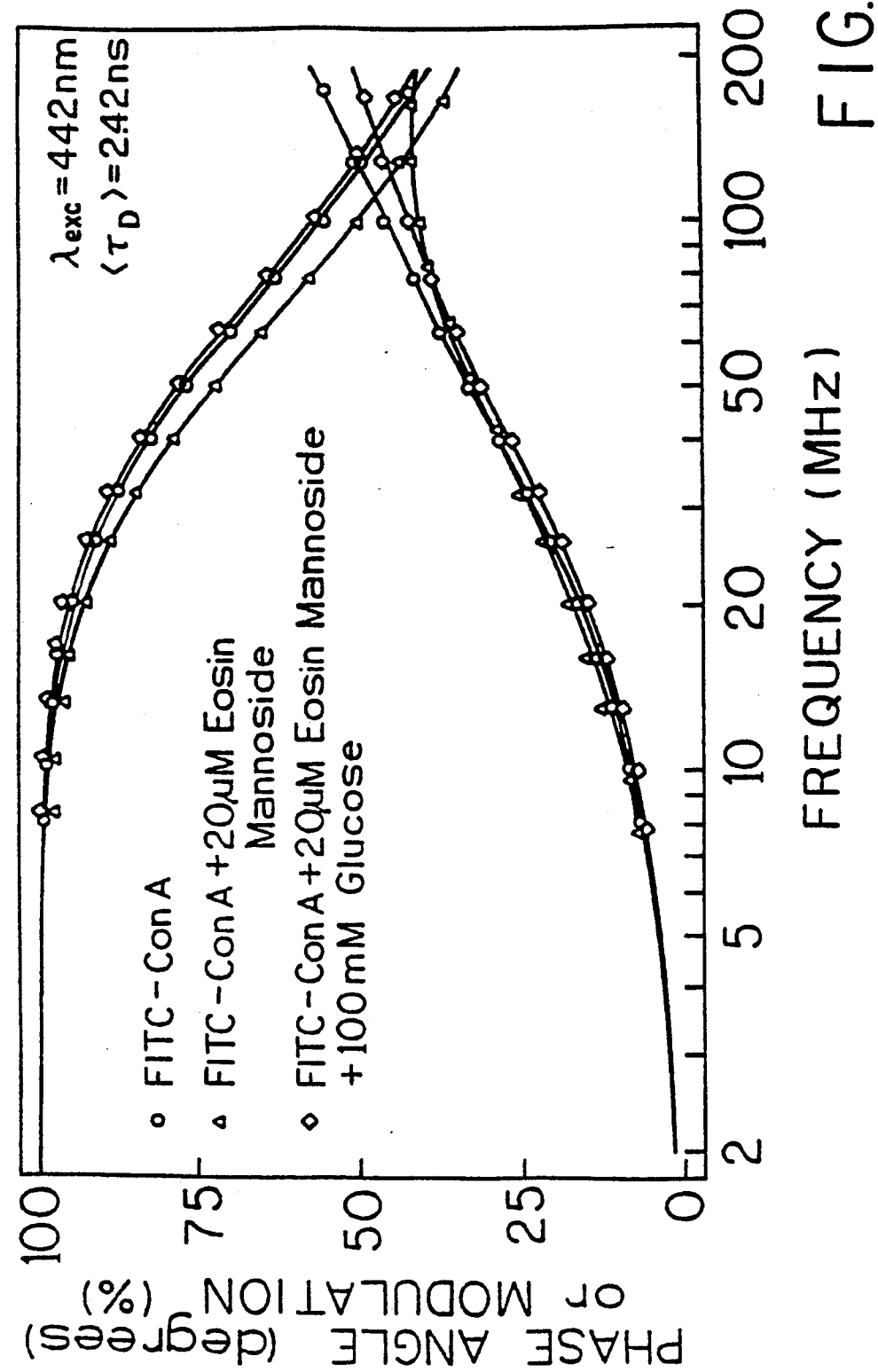

DETERMINATION AND QUANTIFICATION OF SACCHARIDES BY LUMINESCENCE LIFETIMES AND ENERGY TRANSFER

FIELD OF THE INVENTION

The present invention relates to a method of sensing saccharides and, more particularly, to a method of sensing saccharides using luminescent lifetimes and energy transfer.

BACKGROUND OF THE INVENTION

Determination and quantification of glucose, particularly blood glucose, is necessary for the clinical treatment of diabetics. One typical method of measuring glucose concentration includes the use of glucose oxidase followed by electrochemical measurement of $H_2O_2$. However, this method suffers from the disadvantage that it requires an extracted blood sample in order to determine the level of glucose in the blood, and the measurement cannot be accomplished in a non-invasive manner.

Alternatively, it is known to sense glucose using fluorescence intensity measurements. However, fluorescence intensity measurements can be inaccurate and/or imprecise in view of photobleaching, light scattering off the tissues and high absorbance by the blood, which makes these measurements not practical for making reliable measurements of glucose concentration. Furthermore, such measurements are often accomplished by the indirect method of using changes in fluorescence intensity resulting from the consumption of the fluorescence quencher oxygen by glucose oxidase.

SUMMARY OF THE INVENTION

The present invention overcomes the above difficulties by providing a method for the measurement of glucose using luminescence lifetimes and energy transfer. According to the method of the invention, an energy transfer donor-acceptor pair is brought into contact with a sample to be analyzed, the donor of the donor-acceptor pair being photoluminescent. The sample is then illuminated and the resultant emission detected.

One of the donor-acceptor pair is bound to a carrier, while the other of the donor-acceptor pair and any glucose present in the sample compete for binding sites on the carrier. Energy transfer occurs between the donors and the acceptors when they are bound together, which produces a detectable lifetime change of the fluorescence of the donor. The lifetime change is reduced or even eliminated by the competitive binding of glucose. Thus, by measuring the apparent luminescence lifetime, for example, by phase-modulation fluorometry or time-resolved fluorometry, the amount of glucose in the sample can be determined.

In a preferred embodiment, the donor is bound to the carrier ConA, while the acceptor and any glucose present compete for binding sites on the ConA. Thus, the lifetime change is reduced or eliminated by the competitive binding of glucose to the acceptor.

The method of the invention is particularly useful for the accurate measurement of glucose concentration in blood, either using invasive or non-invasive methods. It is contemplated that such non-invasive methods may include the use of implantable patches and external fiber optic sensors. It is also envisioned that the method of the invention may be used to provide a control signal for an insulin delivery device. Moreover, the method of the invention is not limited to glucose sensing in bodily fluids, but may also be used for other applications, such as to detect and measure glucose during food processing or in fermentation reactions. The method of the present invention is also applicable to other saccharides, conjugated saccharides and polysaccharides which may be present in samples, in addition to alphamethylmannoside and glucose. Similarly, other carriers besides concanavalin A may be used, such as lectins, wheat germ agglution and ricin.

BRIEF DESCRIPTION OF THE DRAWINGS

FIG. 11A is a graphical representation of phase angle and modulation factor versus frequency for the donor FITC labelled ConA and the acceptor Eosin labelled mannoside with added glucose;

DETAILED DESCRIPTION OF THE PREFERRED EMBODIMENTS

Figure 1:
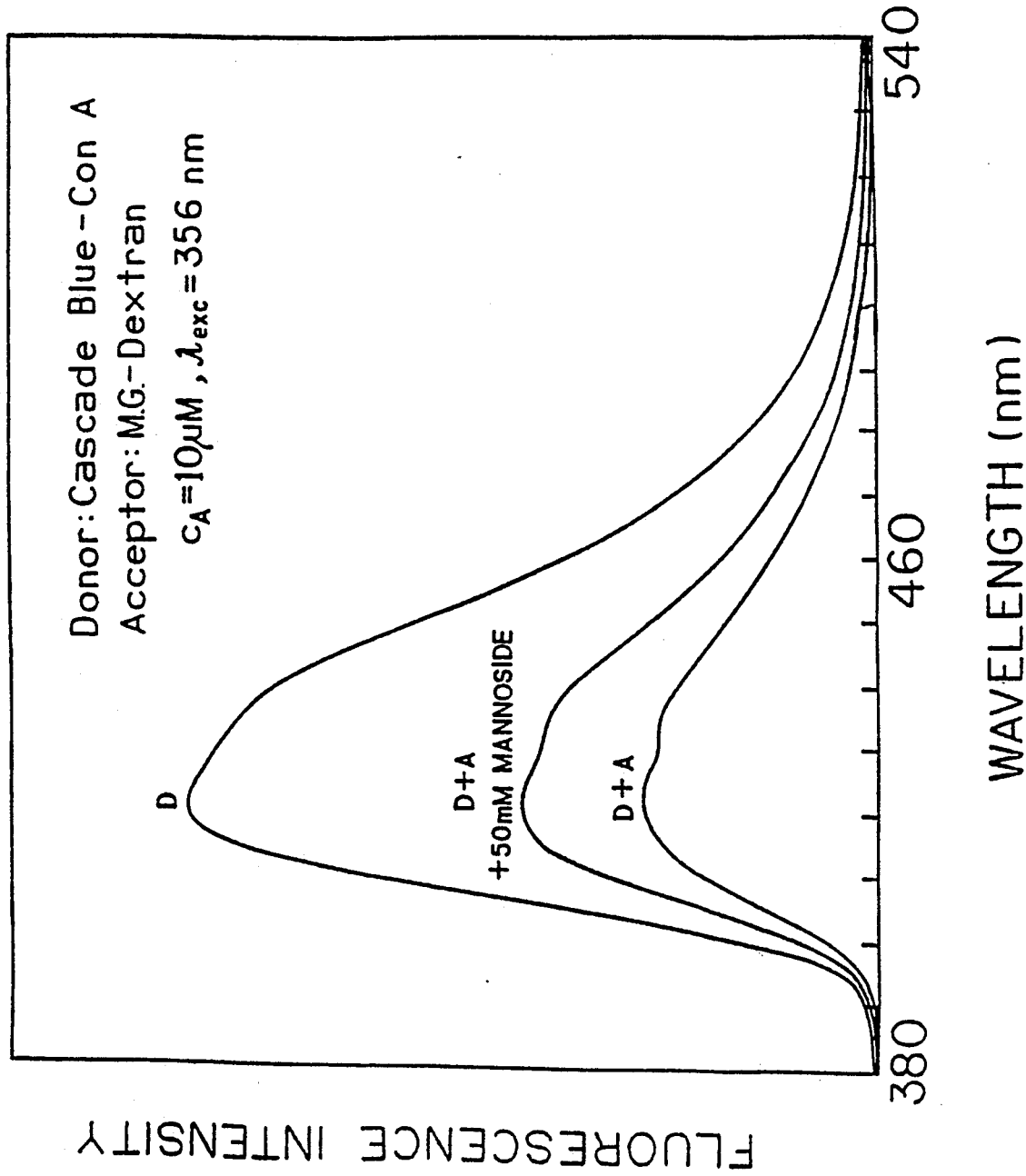
FIG. 1 is a graphical representation of fluorescence intensity versus wavelength for the donor Cascade Blue labelled ConA and the acceptor Malachite Green labelled Dextran showing the donor alone, the donor plus the acceptor, and the donor plus the acceptor and 50mM mannoside.

According to the method of the invention, an energy transfer donor-acceptor pair is exposed or brought into contact with to a sample to be analyzed. For the purposes of the invention, "sample" is to be broadly construed to include any compounds, surfaces, solutions, emulsions, suspensions, mixtures, cell cultures, fermentation cultures, cells, tissues, secretions and/or derivatives or extracts thereof. Measurements in accordance with the method of the invention can be taken in vitro, in vivo and in situ.

In accordance with a preferred embodiment of the invention, the donor of each donor-acceptor pair is fluorescent. Suitable fluorescent donors include Cascade Blue, Texas Red, fluorescein, and 7-amino-4-methylcoumarin-3-carboxylic acid ("AMCA") and esters thereof such as the succinimidyl ester, and longer lived fluorophores, such as lanthanides and metal-ligand complexes. The use of longer-lived fluorophores may be particularly useful in clinical measurements of blood samples because they provide for suppression of autofluorescence from tissue.

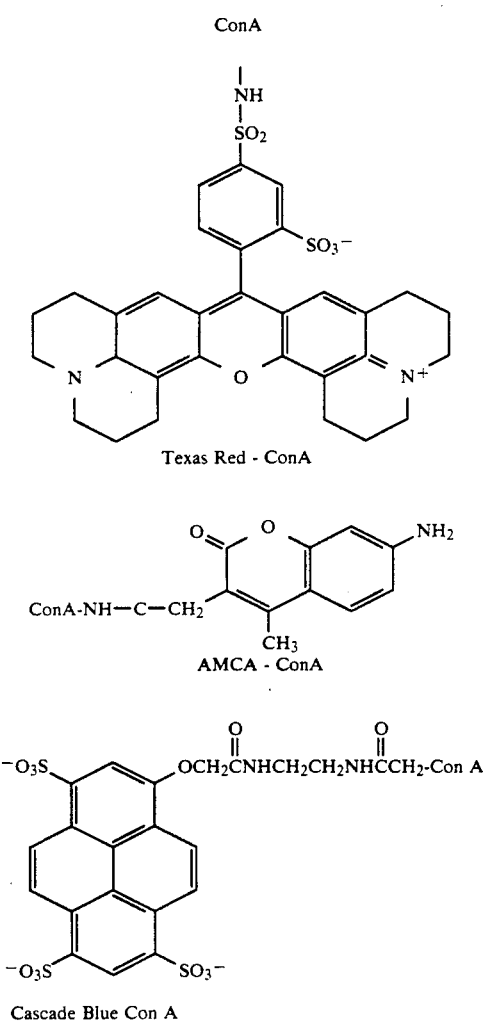

Acceptors may include malachite green, eosin, and TRITC, which may be bound to a carrier, for example malachite green dextran, as shown below.

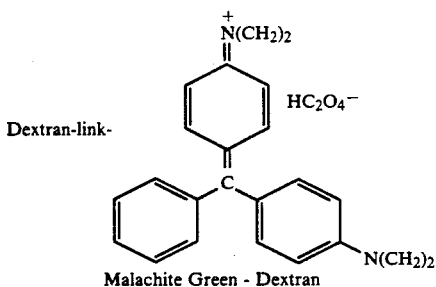

Malachite Green - Dextran

One of the advantages of the use of energy transfer is the ability to selectively shift the excitation and emission wavelengths to longer or shorter wavelengths, as desired. Hence, the invention can use a wide range of light sources, including pulsed or modulated laser diodes, and wavelengths beyond tissue and hemoglobin absorption. Additionally, the use of longer lived fluorophores mentioned above can provide a means to avoid autofluorescence and allow the use of electro-luminescent devices as the light source. Such devices are the subject of U.S. patent application Ser. No. 07/755,232, filed Sept. 5, 1991, the contents of which are incorporated herein by reference.

According to the invention, one of the donor-acceptor pair is bound to a carrier, while the other of the donor-acceptor pair and any glucose present in the sample compete for binding sites on the carrier. In a preferred embodiment, the donor is bound to the carrier and the acceptor competes with glucose for binding sites on the carrier. In this way, the carrier can be said to be "labelled" with the donor. It is important that the donor itself not be glucose sensitive, or it will interfere with the competitive displacement between glucose and the donor. A carrier which has been found to be particularly useful when bound to the fluorescent donor for purposes of the invention is Concanavalin A (ConA). The succinyl derivative of ConA may be particularly useful in view of its increased stability and resistance to self-aggregation.

It is also envisioned that the acceptor may be bound to a different carrier, such as a sugar or a polymeric sugar. Thus, the sugar or polymeric sugar can be said to be "labelled" with the acceptor. This is advantageous because it prevents the loss of the acceptor, for example, from an implantable patch wherein the sensor region in contact with the patch is permeable to glucose. Labelled sugars or polymeric sugars useful in the method of the invention include Malachite Green-Dextran, eosin cadaverine-alpha, TRITC-mannoside and TRITC-cadaverine-alpha, D-mannose pyranosyl phenyl.

The method of the invention further includes the steps of illuminating the sample and detecting the resultant emission. One of the advantages of using an energy transfer donor-acceptor pair is that any suitable light source may be used, as long as the light source can be directly or externally modulated. Light sources for use in the invention thus include ion lasers, dye lasers, LED's, laser diodes, ELL's, and the like. Filters may be used to filter the incident beam as well as the emitted beam, as necessary to obtain desired wavelengths.

In accordance with the present invention, energy transfer occurs between the donor and the acceptor, at least one of which is photoluminescent, as mentioned above. Energy transfer between the donor and acceptor causes a change in the fluorescent lifetime corresponding to the presence of glucose. It is to be noted that the efficiency of the energy transfer depends on the quantum Yield of the donor, the overlapping of the emission spectrum of the donor with the absorption spectrum of the acceptor, and the relative distance and orientation between the donor and the acceptor.

In a preferred embodiment, the intensity of the excitation radiation is modulated at a particular modulation frequency and the lifetime determined using known phase-modulation, i.e., frequency-domain, techniques. Alternatively, a pulsed radiation source may be used and the lifetime of the sample determined using known time-resolved methods. Both phase-modulation and time-resolved fluorometry methods are well known in the prior art, see Lakowicz, *Principles of Fluorescence Spectroscopy*, Plenum Press, 1983, Chapter 3. However, current instrumentation renders the phase-modulation method more expedient. For the sake of conciseness, only the phase-modulation method will be discussed further herein, but it is understood that these same principles generally apply to time-resolved measurements.

When the sample is excited with radiation whose intensity is modulated, for example, in a sinusoidal manner, the time lag between absorption and emission causes the emission to be delayed in phase and demodulated relative to the excitation radiation. This phase shift $\phi$ and the corresponding demodulation factor m are used to measure and calculate the photoluminescent lifetime based on well known formulae. See, Lakowicz, supra.

This phase shift can be measured using conventional instrumentation, including, for example, that disclosed in U.S. Pat. No. 4,937,457 to Mitchell, and that disclosed in Lakowicz, "A Review of Photon-Counting and Phase-Modulation Measurements of Fluorescence Decay Kinetics", *Applications of Fluorescence in the Biomedical Sciences*, pp. 29–67 (1986), the contents of which are incorporated herein by reference.

The invention is further illustrated by the following examples:

EXAMPLE 1

ConA was labelled with three different donors. Experiments were performed using the labelled ConA's and the acceptor-labelled polymeric sugar malachite green-dextran (molecular weight 10,000). The labelling of the dextran was carried out in 0.1 M carbonate buffer, with a pH of 9.2. The malachite green-dextran (MG-D) was obtained by dissolving about 10 mg amino dextran in 0.5 ml of buffer and mixing with 50ml of tenfold molar excess over amines of malachite green isothiocyanate dissolved in DMSO. The reaction was allowed to proceed for four hours at room temperature. The labelled dextran was separated from free dye by passage through a sephadex G-50 column.

Experiments showed that the fluorescence of the donor Cascade Blue carried by ConA is quenched by the binding of MG-D to ConA. Quenching was partially reversed by the addition of an unlabelled sugar, methylmannoside, which shows the effects of the competition for binding sites on the ConA. The results are shown in FIG. 1.

EXAMPLE 2

Figure 2:
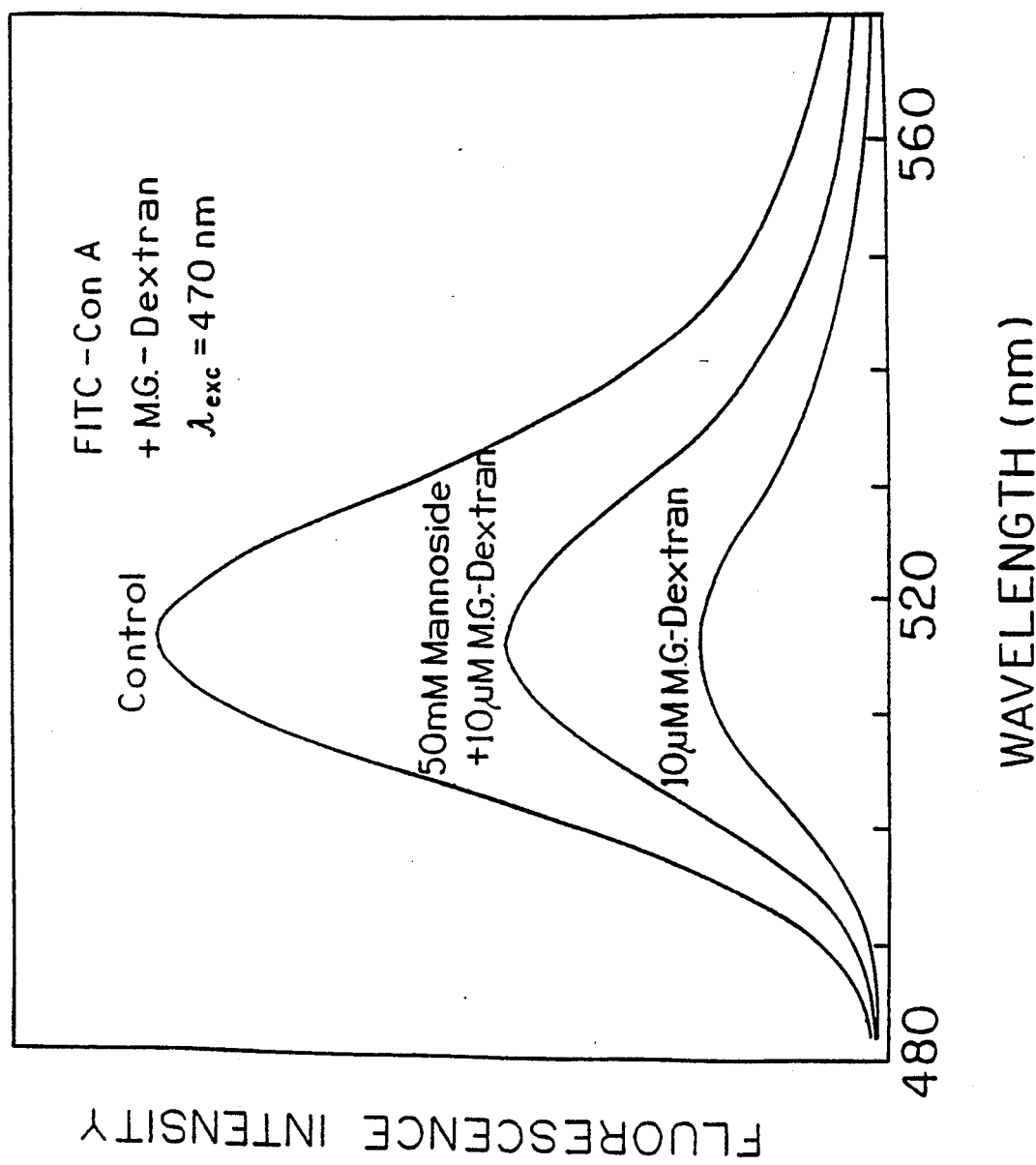
FIG. 2 is a graphical representation of fluorescence intensity versus wavelength for the donor FITC labelled ConA and the acceptor Malachite Green labelled Dextran showing a control (the donor alone). the donor plus the acceptor, and the donor plus the acceptor and 50mM mannoside.

Further experiments were conducted using MG-D as prepared in Example 1. The experiments showed that the fluorescence of the donor fluorescein carried by ConA is quenched by the binding of MG-D to ConA. Quenching was partially reversed by the addition of an unlabelled sugar, methylmannoside, which shows the effects of the competition for binding sites on the ConA. The results are shown in FIG. 2.

EXAMPLE 3

Figure 3:
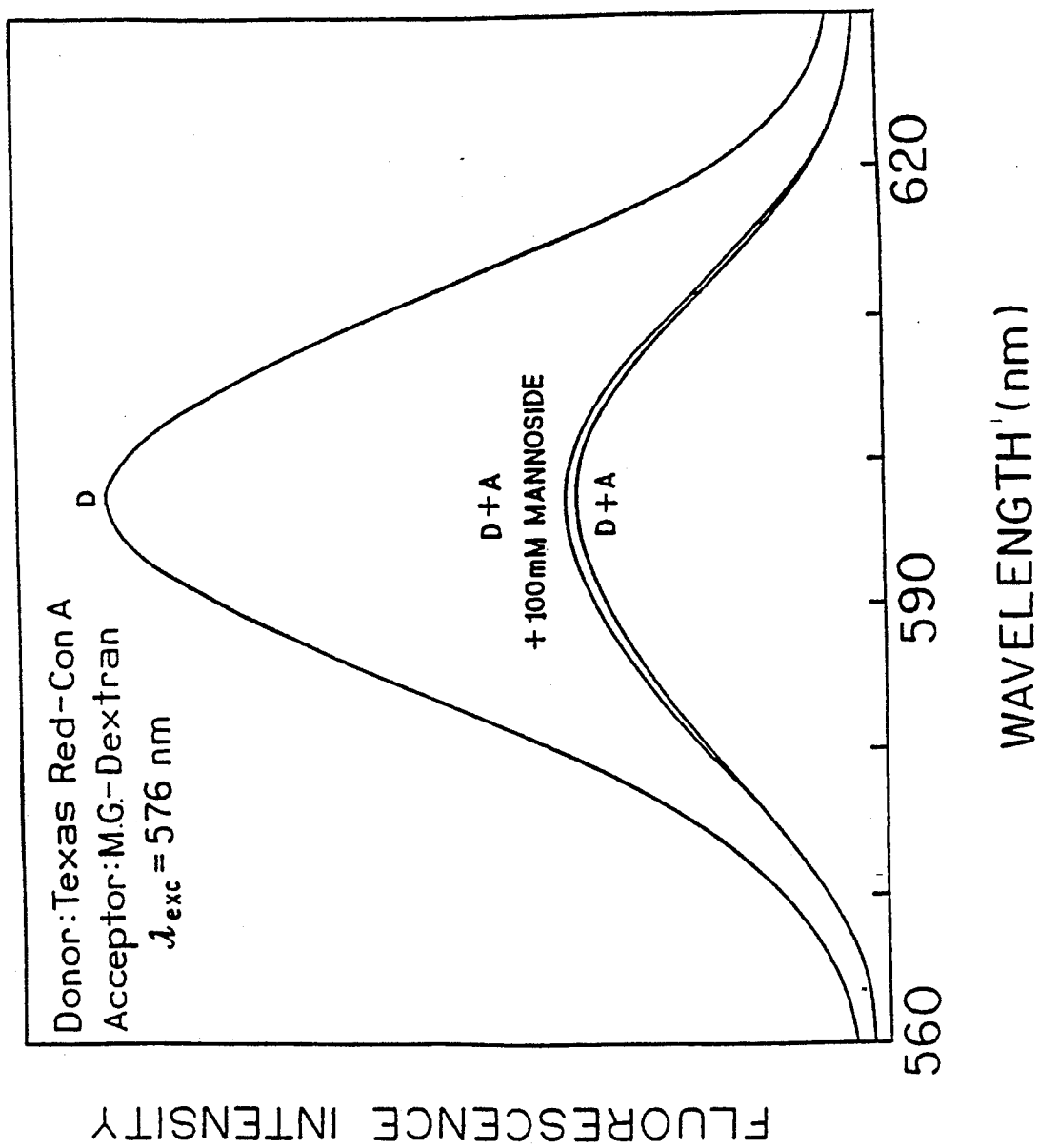
FIG. 3 is a graphical representation of fluorescence intensity versus wavelength for the donor Texas Red labelled ConA and the acceptor Malachite Green labelled Dextran showing the donor alone, the donor plus the acceptor, and the donor plus the acceptor and 100 mM mannoside.
Figure 3A:
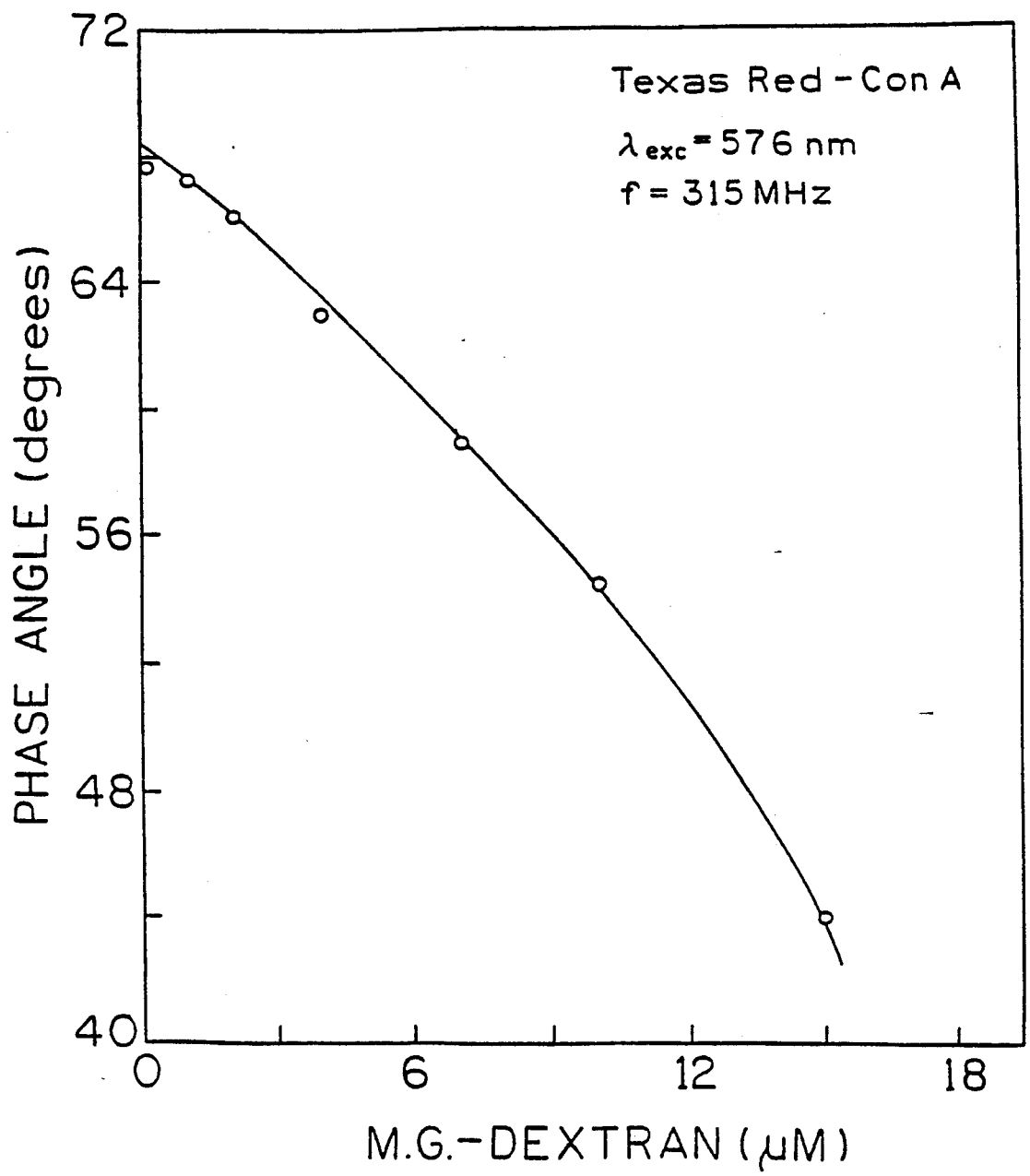
FIG. 3A is a graphical representation of phase angle versus concentration of Malachite Green labelled Dextran for the donor Texas Red labelled ConA.

Further experiments were conducted using MG-D as prepared in Example 1. The experiments showed that the fluorescence of the donor Texas Red carried by ConA is quenched by the binding of MG-D to ConA. Quenching was partially reversed by the addition of an unlabelled sugar, methylmannoside, which shows the effects of the competition for binding sites on the ConA, but the reversal was modest. The results are shown in FIG. 3. The effects of the acceptor on the phase angle are shown in FIG. 3A, which shows the decrease in phase angle with increasing acceptor concentration. The phase angles of the donor were thus found to be a more sensitive indication of ConA-sugar interactions than was the steady state intensity.

EXAMPLE 4

Figure 4:
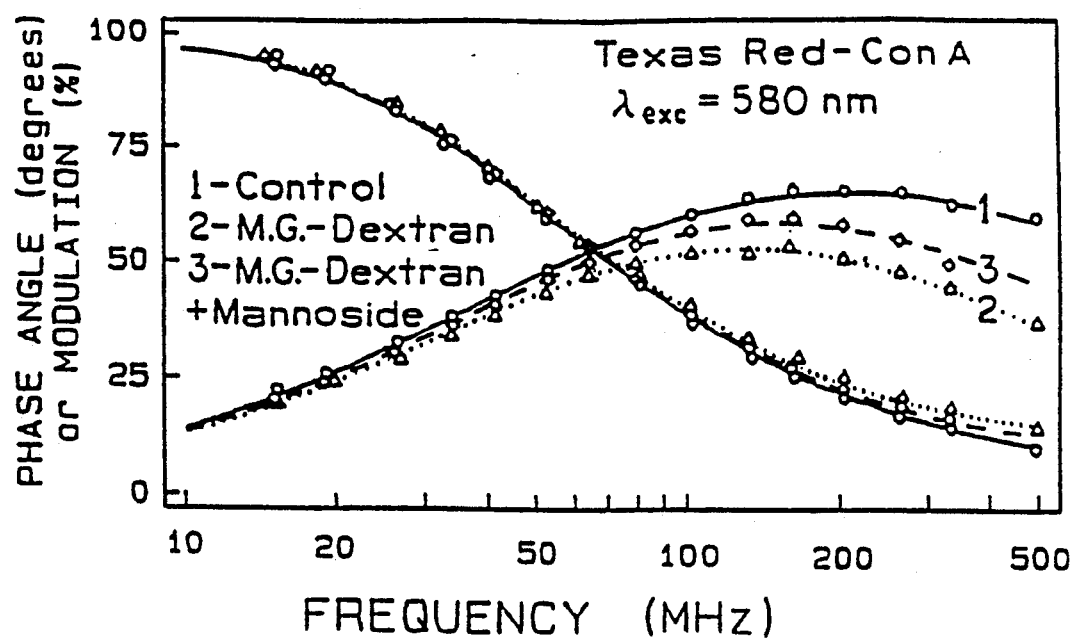
FIG. 4 is a graphical representation of phase angle and modulation factor versus frequency for the donor Texas Red labelled ConA alone, the donor Texas Red labelled ConA and the acceptor Malachite Green labelled Dextran, and the donor Texas Red labelled ConA and the acceptor Malachite Green labelled Dextran plus mannoside.
Figure 5:
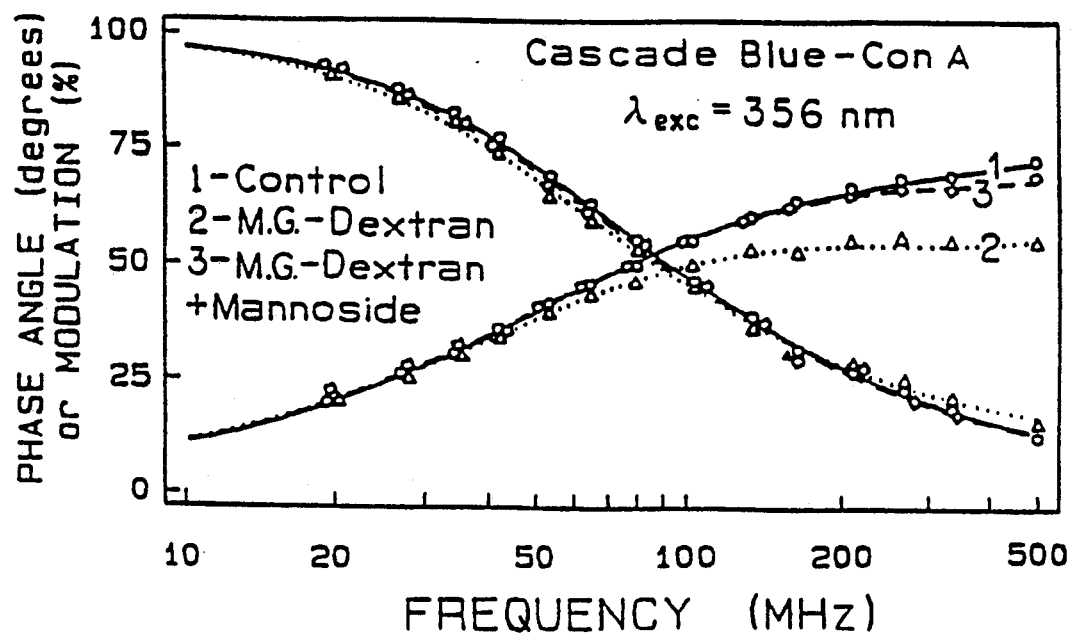
FIG. 5 is a graphical representation of phase angle and modulation factor versus frequency for the donor Cascade Blue labelled ConA alone, the donor Cascade Blue labelled ConA and the acceptor Malachite Green labelled Dextran and the donor Cascade Blue labelled ConA and the acceptor Malachite Green labelled Dextran plus mannoside.
Figure 6:
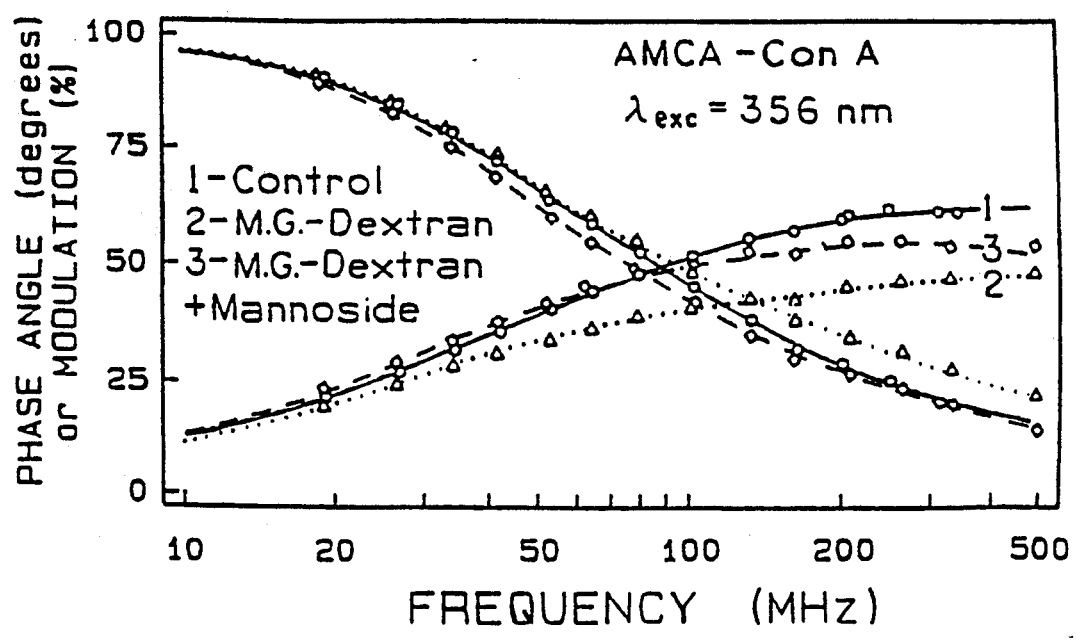
FIG. 6 is a graphical representation of phase angle and modulation factor versus frequency for the donor AMCA labelled ConA alone, the donor AMCA labelled ConA and the acceptor Malachite Green labelled Dextran and the donor AMCA labelled ConA and the acceptor Malachite Green labelled Dextran plus mannoside.

Further experiments were conducted using MG-D as prepared in Example 1. The experiments showed that phase angles decreased at a modulation frequency of 100-500 MHz for each of the donors AMCA, Cascade Blue and Texas Red carried by ConA in the presence of MG-D. These decreases were partially reversed by the addition of an unlabelled sugar, methylmannoside, which shows the effects of the competition for binding sites on the ConA. The results are shown in FIGS. 4-6.

EXAMPLE 5

Figure 7:
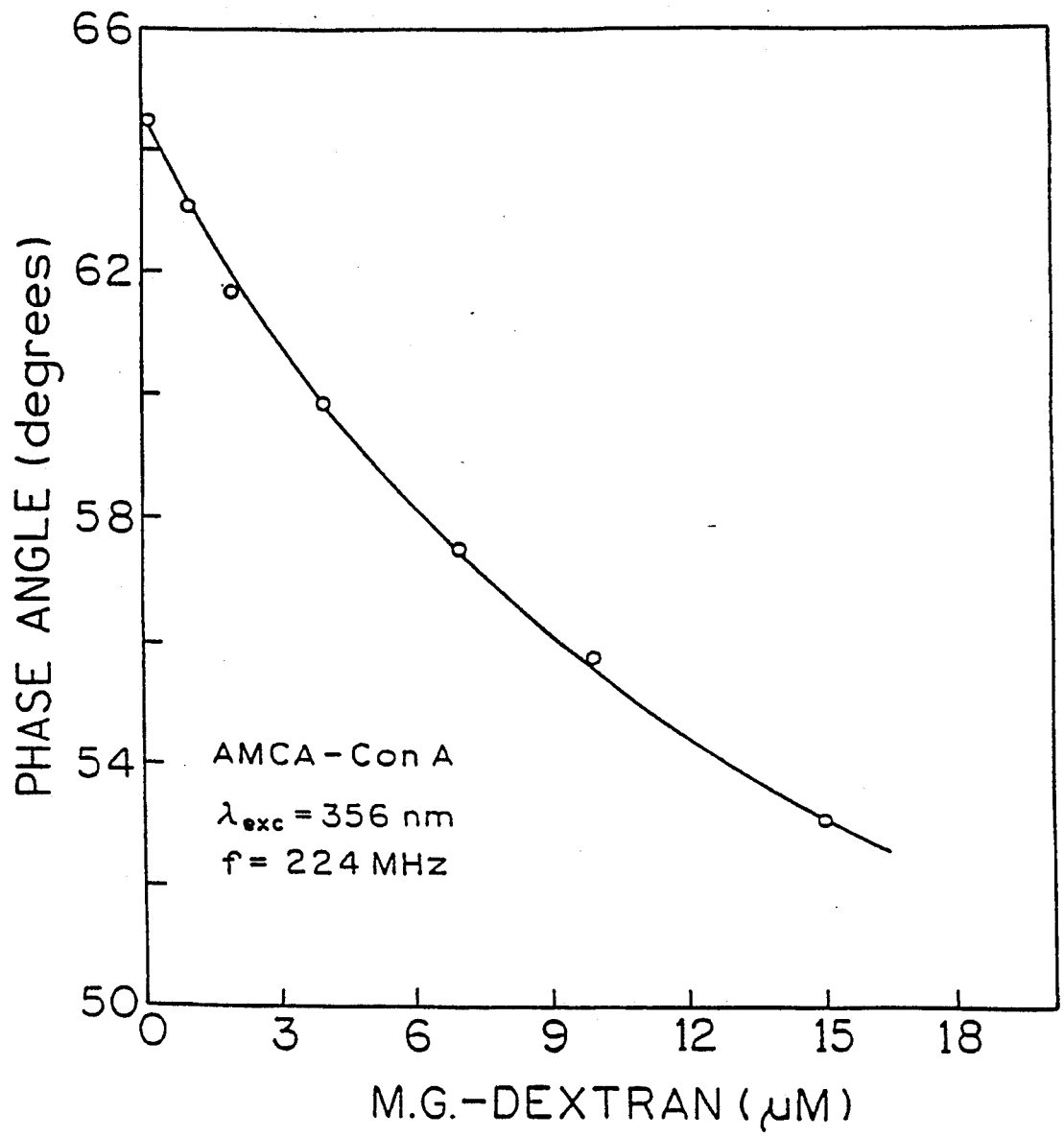
FIG. 7 is a graphical representation of phase angle versus concentration of Malachite Green label? ed Dextran for the donor AMCA labelled ConA; the insert shows the effect of added mannoside on the phase angle of AMCA labelled ConA with malachite green labelled dextran.
Figure 7A:
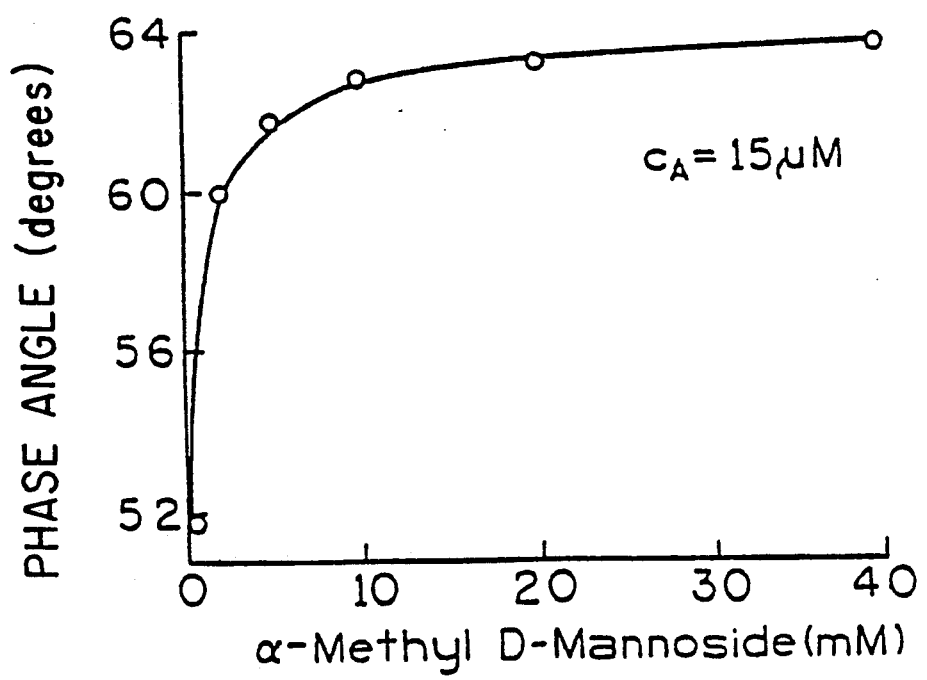

Further experiments were conducted using MG-D as prepared in Example 1. The donor was AMCA-ConA. The results are shown in FIG. 7, which shows the decrease in phase angle observed with increasing amounts of acceptor. This effect was reversed by the addition of the unlabelled sugar methylmannoside, as shown in the insert of FIG. 7.

EXAMPLE 6

Experiments were conducted using eosin-mannoside instead of MG-D. Although not shown in the Figures, these experiments showed that the fluorescence of the donor Cascade Blue carried by ConA is quenched by the binding of the acceptor-labelled sugar eosin-mannoside to ConA. Quenching was partially reversed by the addition of glucose, which shows the effects of the competition for binding sites on the ConA.

The experiments further showed that phase angles decreased at a modulation frequency of 100-200 MHz. These decreases were partially reversed by the addition of glucose.

EXAMPLE 7

Experiments were conducted as in Example 4, except that the donor was fluorescein instead of Cascade Blue. Although not shown in the Figures, these experiments showed that the fluorescence of the donor fluorescein carried by ConA is quenched by the binding of the acceptor-labelled sugar eosin-mannoside to ConA. Quenching was partially reversed by the addition of glucose, which shows the effects of the competition for binding sites on the ConA.

The experiments further showed modest decreases in phase angle at a modulation frequency of 100-200 MHz. These decreases were partially reversed by the addition of glucose.

EXAMPLE 8

Figure 8:
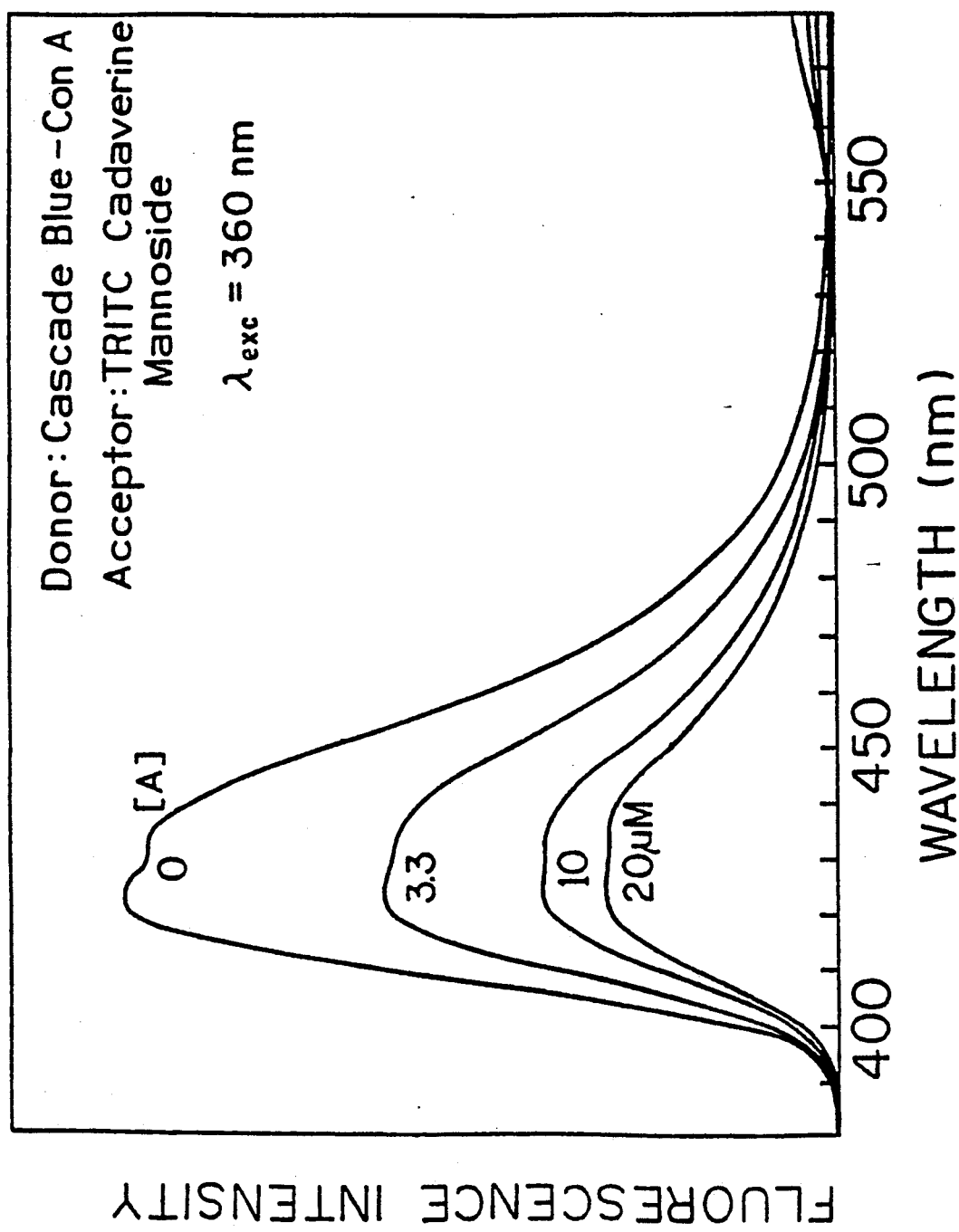
FIG. 8 is a graphical representation of fluorescence intensity versus wavelength for the donor Cascade Blue labelled ConA and the acceptor TRITC Cadaverine labelled mannoside for varying amounts of mannoside.

The effect of the acceptor TRITC Cadaverine mannoside on Cascade Blue-labelled ConA was studied. As seen in FIG. 8, the acceptor quenched the fluorescence of the donor, with the effect being more pronounced with increasing acceptor concentration.

EXAMPLE 9

Figure 9:
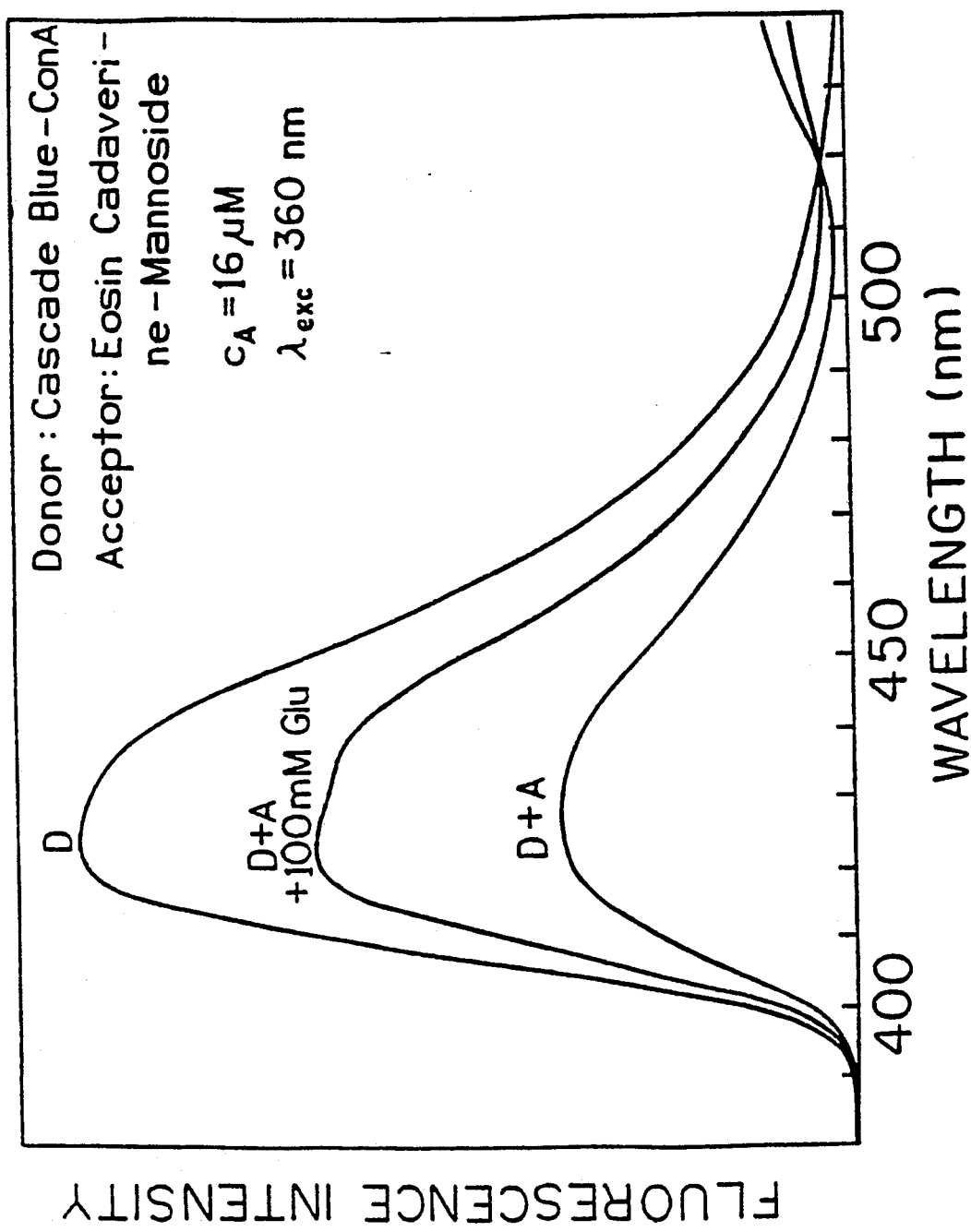
FIG. 9 is a graphical representation of fluorescence intensity versus wavelength for the donor Cascade Blue labelled ConA and the acceptor Eosin Cadaverine labelled mannoside for varying amounts of glucose.
Figure 10A:
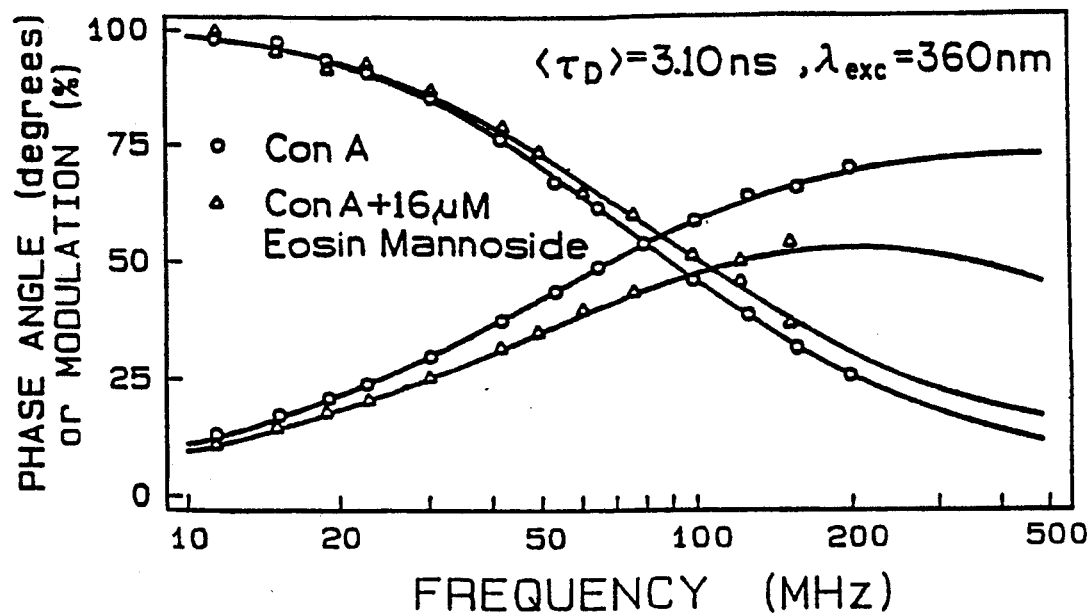
FIG. 10 is a graphical representation of phase angle and modulation factor versus frequency for the donor Cascade Blue labelled ConA and the acceptors TRITC Cadaverine labelled mannoside and Eosin Cadaverine labelled mannoside in the presence of glucose.
Figure 10B:
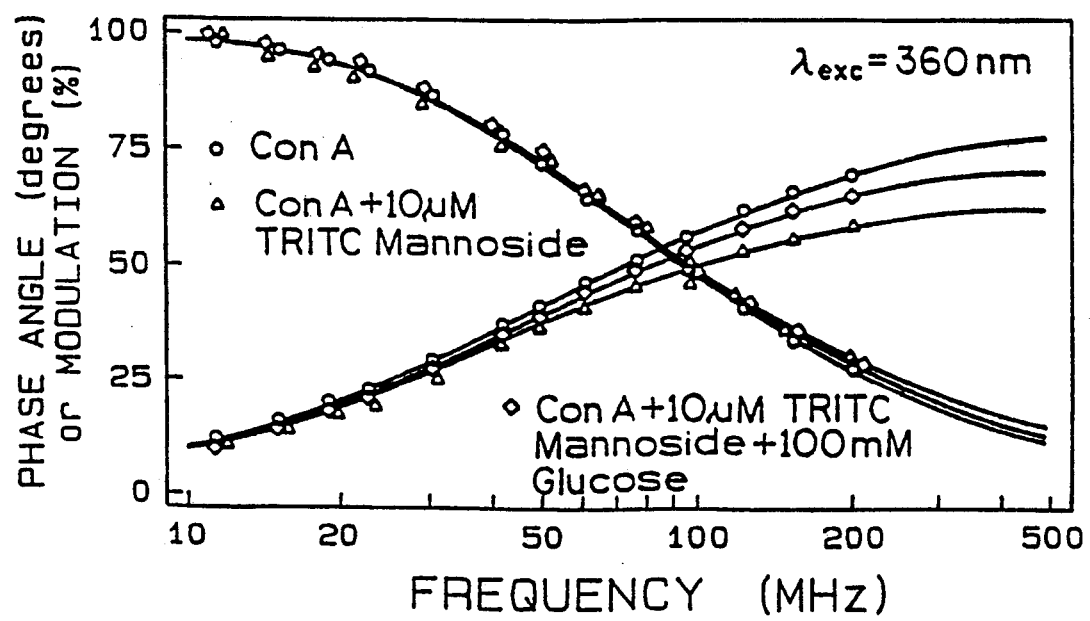

The effect of the acceptor eosin cadaverine mannoside on Cascade Blue-labelled ConA was studied. As seen in FIG. 9, the acceptor quenched the fluorescence of the donor. It can be seen in FIG. 9 that the quenching effect was reversed by glucose. The effect of the acceptor on the relationship between phase angle and modulation and frequency is shown in FIG. 10.

EXAMPLE 10

Figure 11:
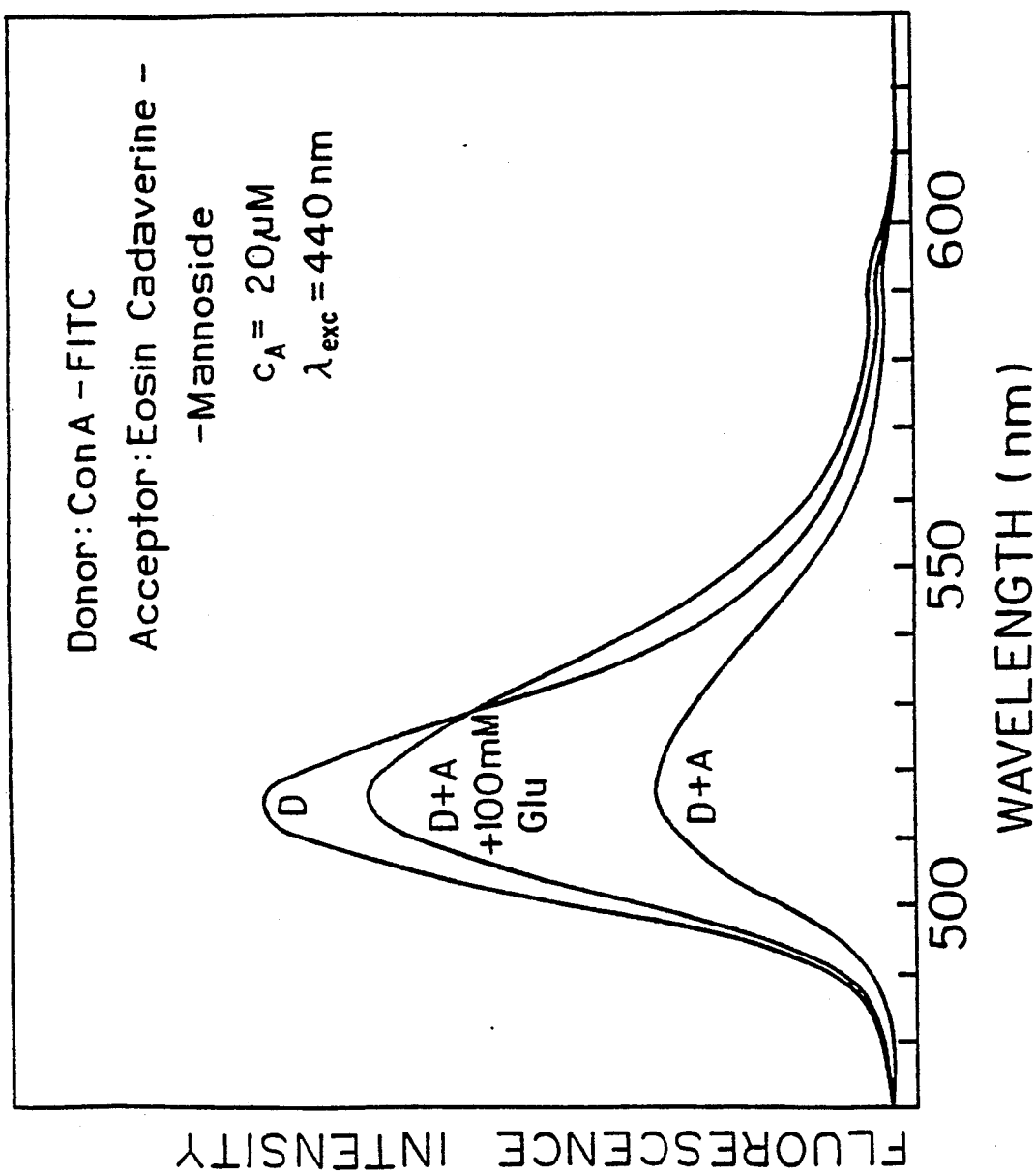
FIG. 11 is a graphical representation of fluorescence intensity versus wavelength for the donor FITC labelled ConA and the acceptor Eosin Cadaverine labelled mannoside for varying amounts of mannoside.

This study was similar to that of Example 9, except the donor was fluorescein-labelled ConA. It can be seen from FIG. 11 that a similar quenching effect was observed, with the quenching again being reversed by the presence of glucose. The effect of the acceptor on the relationship between phase angle and modulation and frequency is shown in FIG. 11A.

EXAMPLE 11

Figure 12:
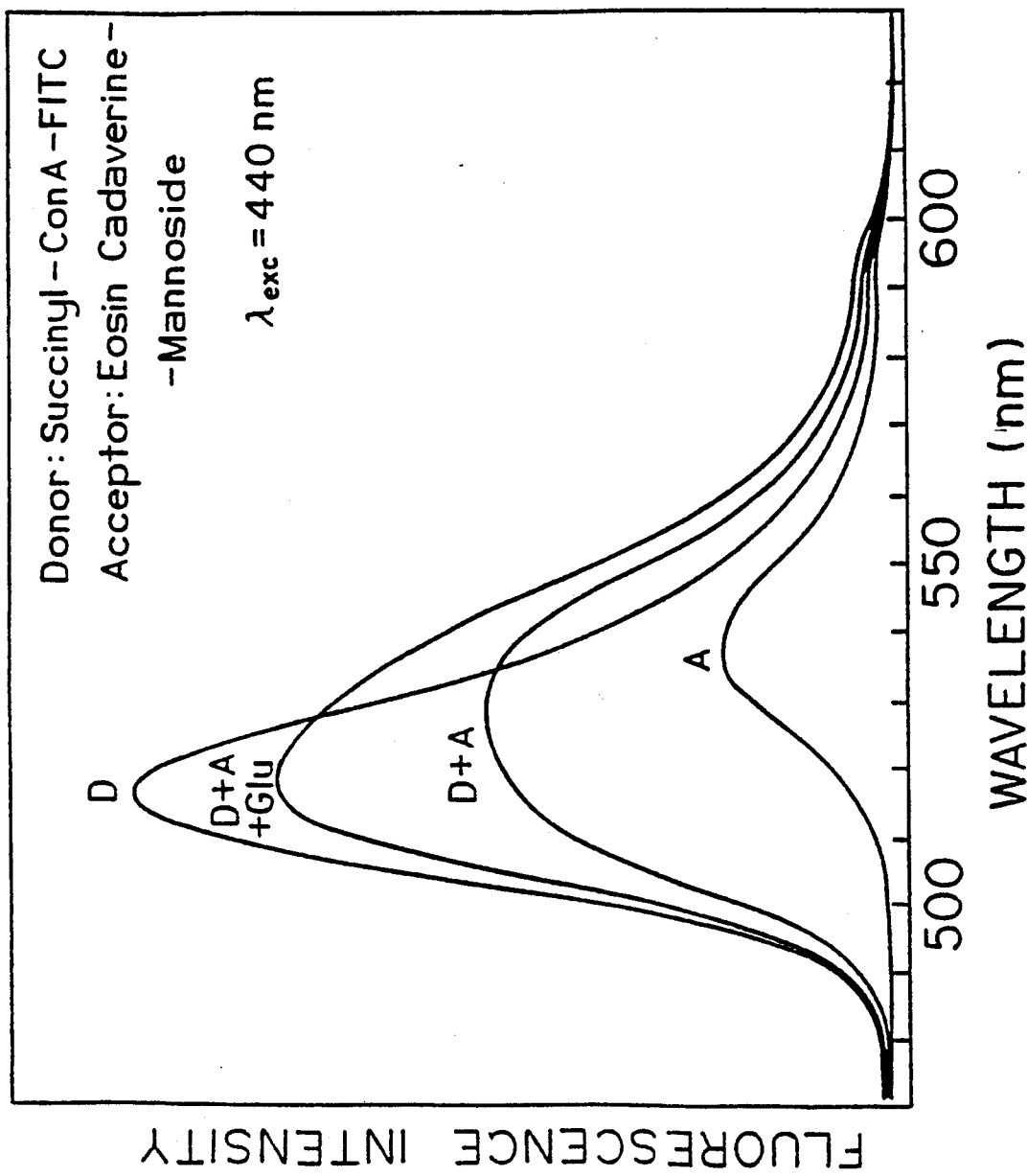
FIG. 12 is a graphical representation of fluorescence intensity versus wavelength for the donor FITC labelled Succinyl-ConA and the acceptor Eosin Cadaverine labelled mannoside for varying amounts of glucose.

This study was similar to that of Example 10, except that the donor was succinyl-ConA-FITC instead of ConA-FITC. It can be seen from FIG. 12 that a similar quenching effect was observed, with the quenching again being reversed by the presence of glucose.

EXAMPLE 12

Figure 13:
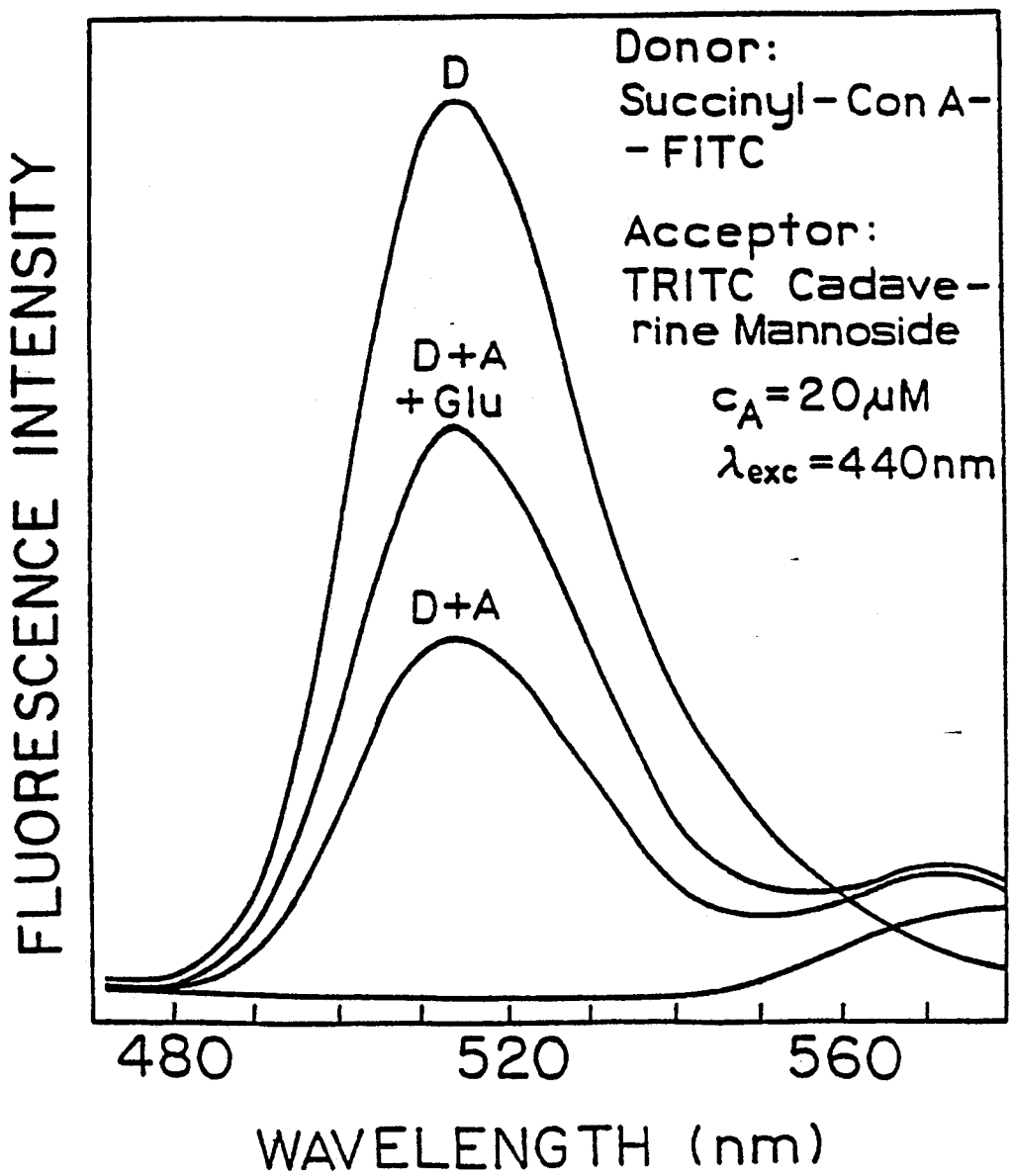
FIG. 13 is a graphical representation of fluorescence intensity versus wavelength for the donor FITC labelled Succinyl-ConA and the acceptor TRTIC Cadaverine labelled mannoside for varying amounts of glucose.

This study was similar to that of Example 11, except that the acceptor was TRITC cadaverine mannoside instead of eosin cadaverine mannoside. It can be seen from FIG. 13 that a similar quenching effect was observed, with the quenching again being reversed by the presence of glucose.

EXAMPLE 13

Figure 14:
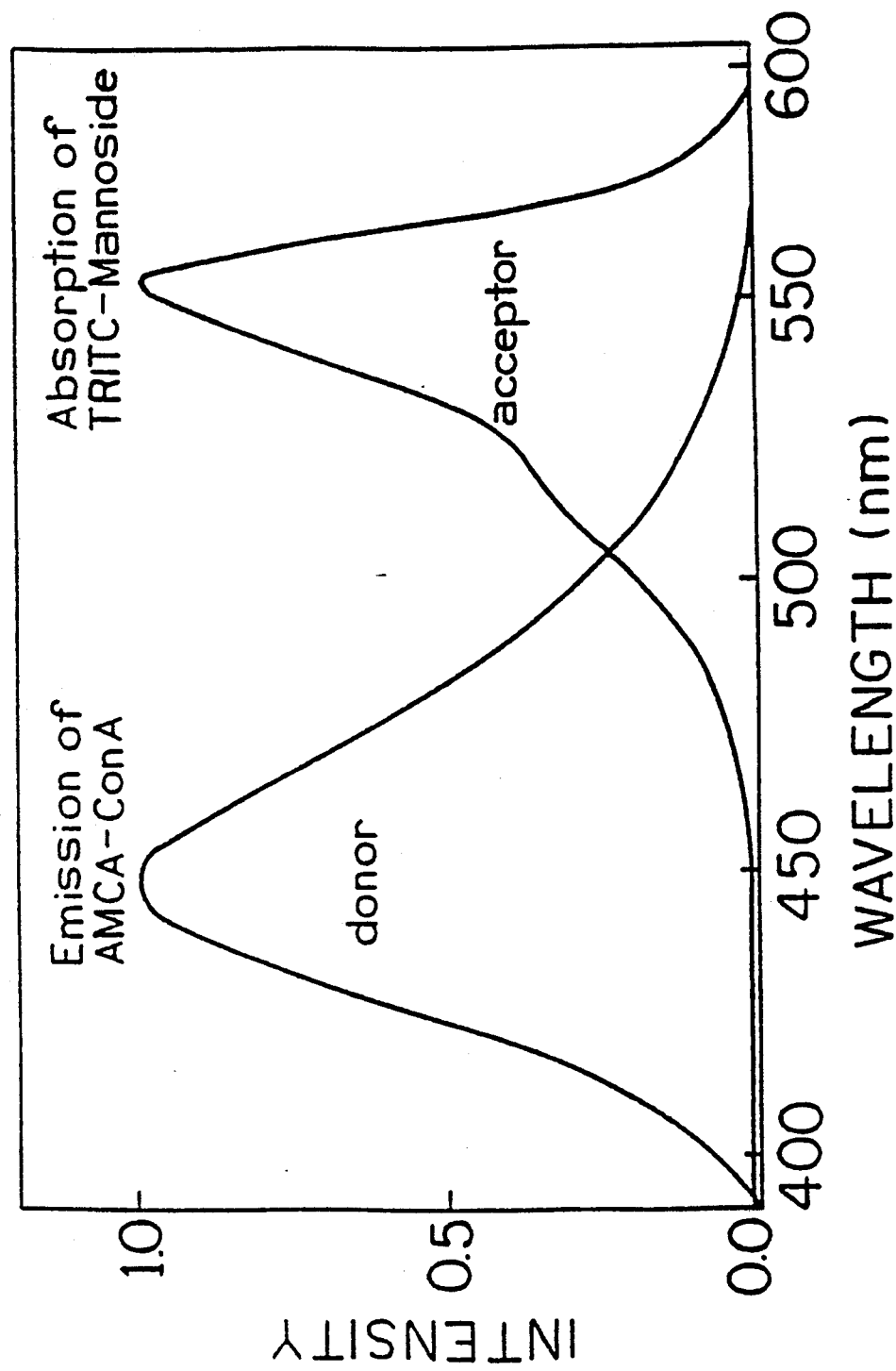
FIG. 14 is a graphical representation of intensity versus wavelength showing the emission spectrum of the donor AMCA labelled ConA and the absorption spectrum of the acceptor TRITC labelled mannoside.
Figure 15:
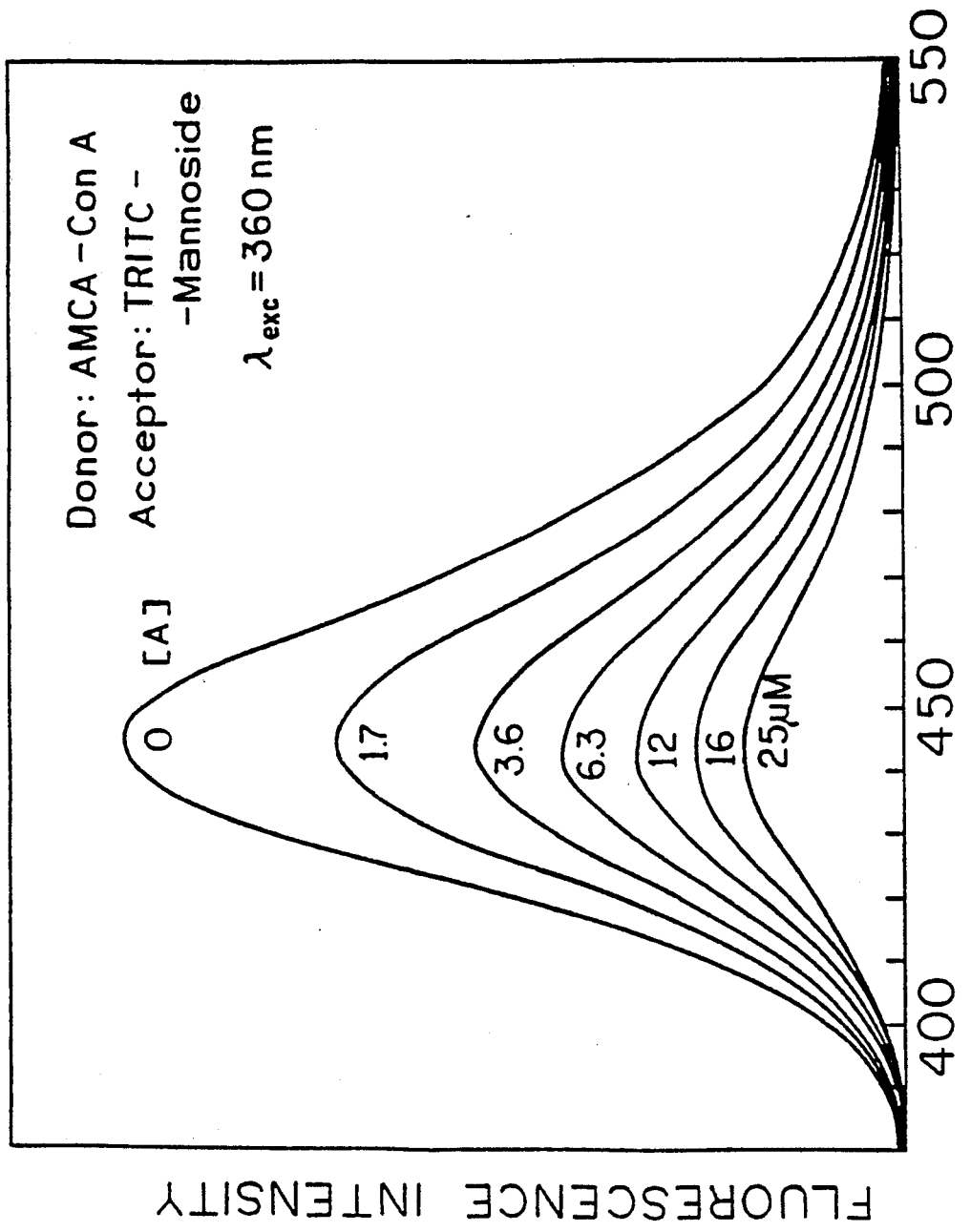
FIG. 15 is a graphical representation of fluorescence intensity versus wavelength for the donor AMCA labelled ConA and the acceptor TRITC labelled mannoside for varying amounts of TRITC-labelled mannoside.
Figure 16:
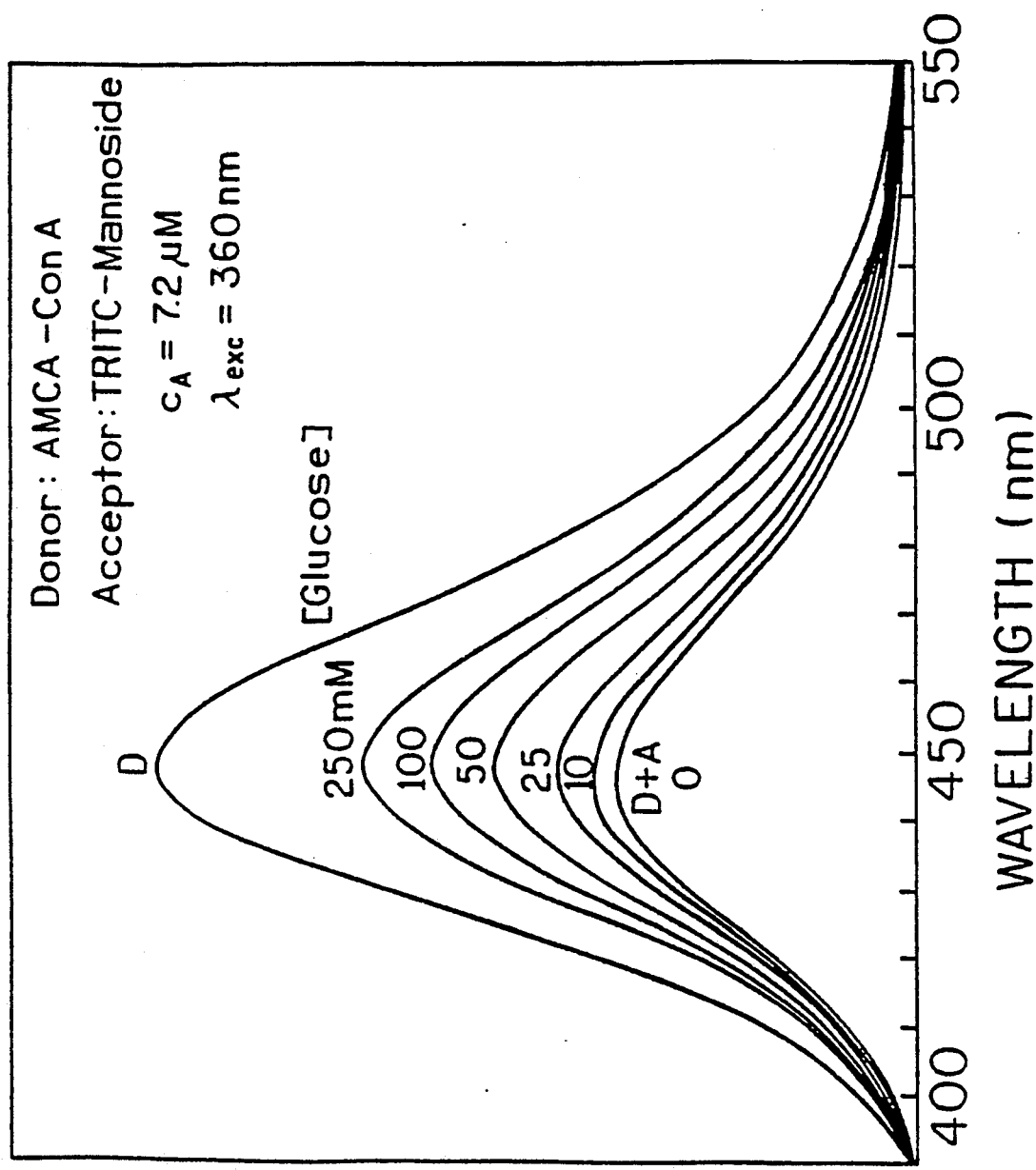
FIG. 16 is a graphical representation of fluorescence intensity versus wavelength for the donor AMCA labelled ConA and the acceptor TRITC labelled mannoside for varying amounts of glucose.
Figure 17:
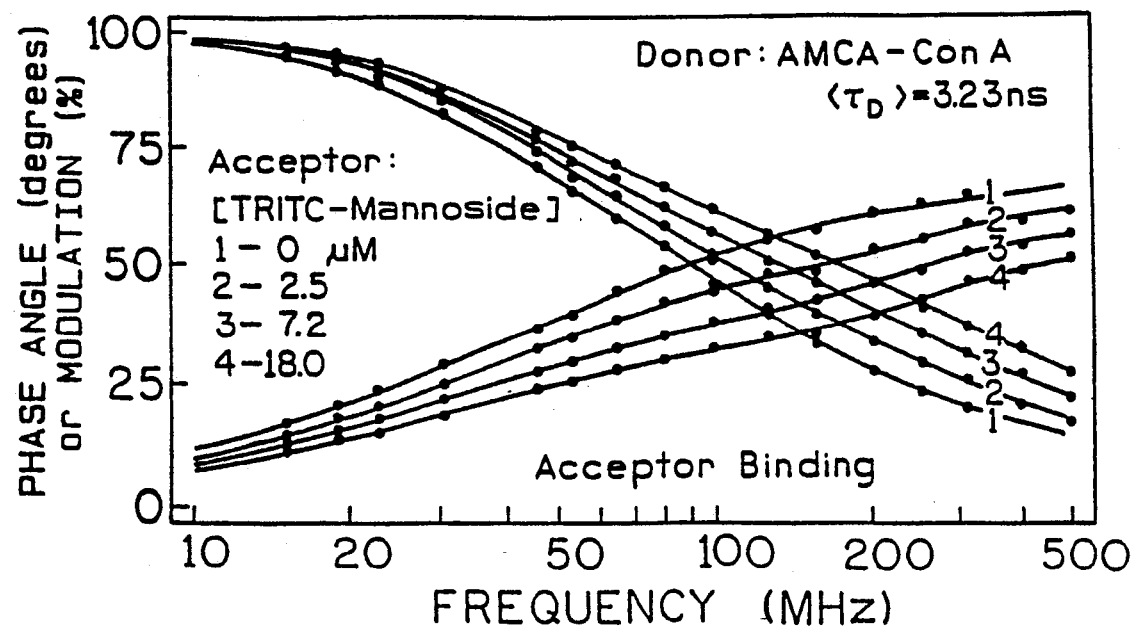
FIG. 17 is a graphical representation of phase angle and modulation factor versus frequency for the donor AMCA labelled ConA and varying amounts of the acceptor TRITC labelled mannoside.
Figure 18:
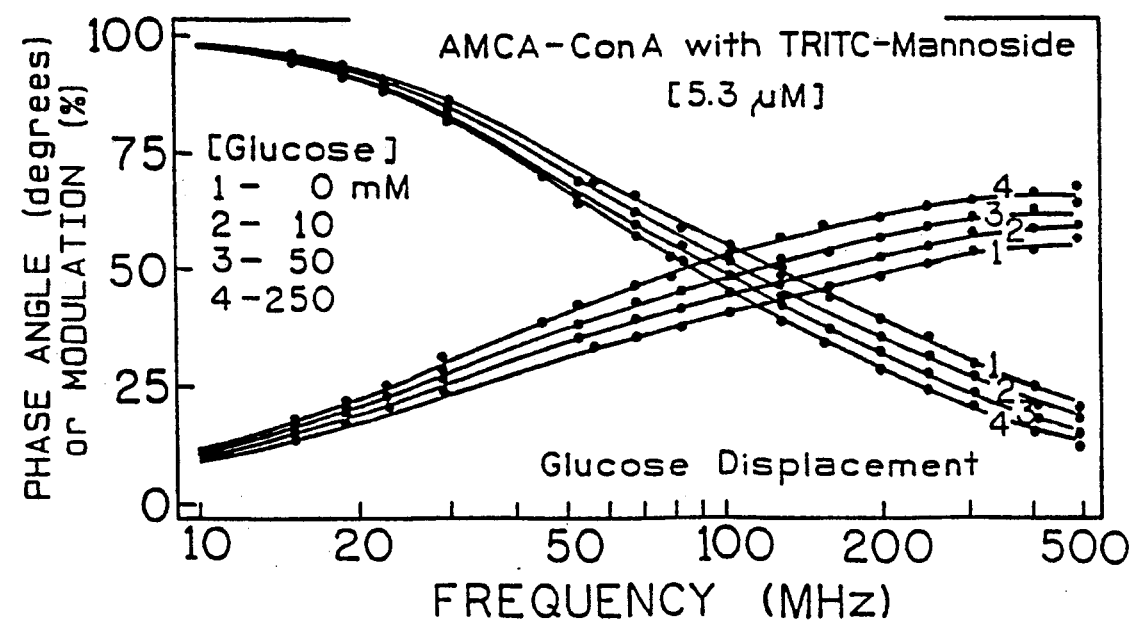
FIG. 18 is a graphical representation of phase angle and modulation factor versus frequency for the donor AMCA labelled ConA and the acceptor TRITC labelled mannoside and varying amounts of glucose.
Figure 19:
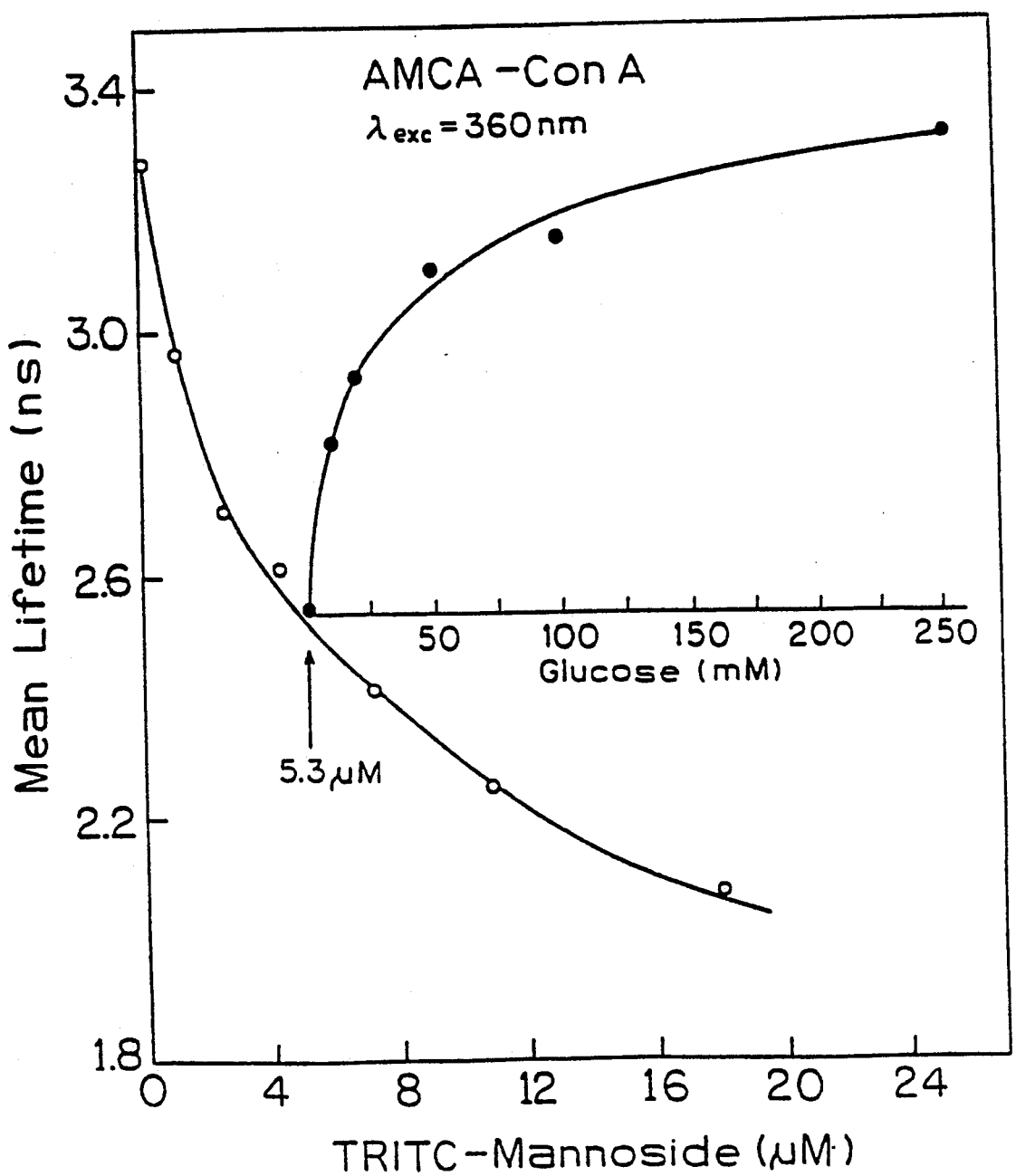
FIG. 19 is a graphical representation of the mean lifetime versus the concentration of the acceptor TRITC labelled mannoside for the donor AMCA labelled ConA the insert in the figure shows the effect of added glucose.
Figure 20:
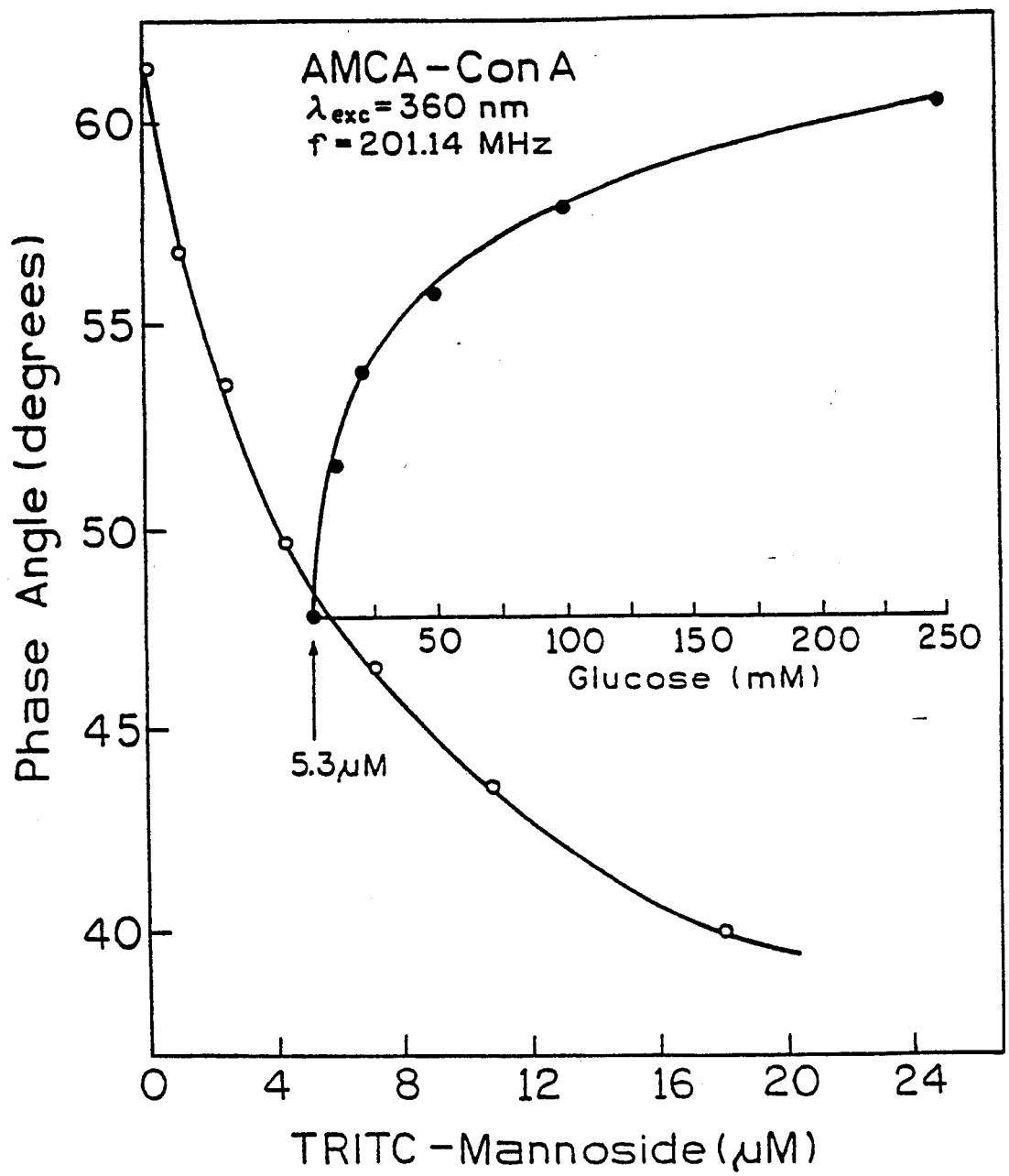
FIG. 20 is a graphical representation of the phase angle versus the concentration of the acceptor TRITC labelled mannoside for the donor AMCA labelled ConA; the insert in the figure shows the effect of added glucose.
Figure 21:
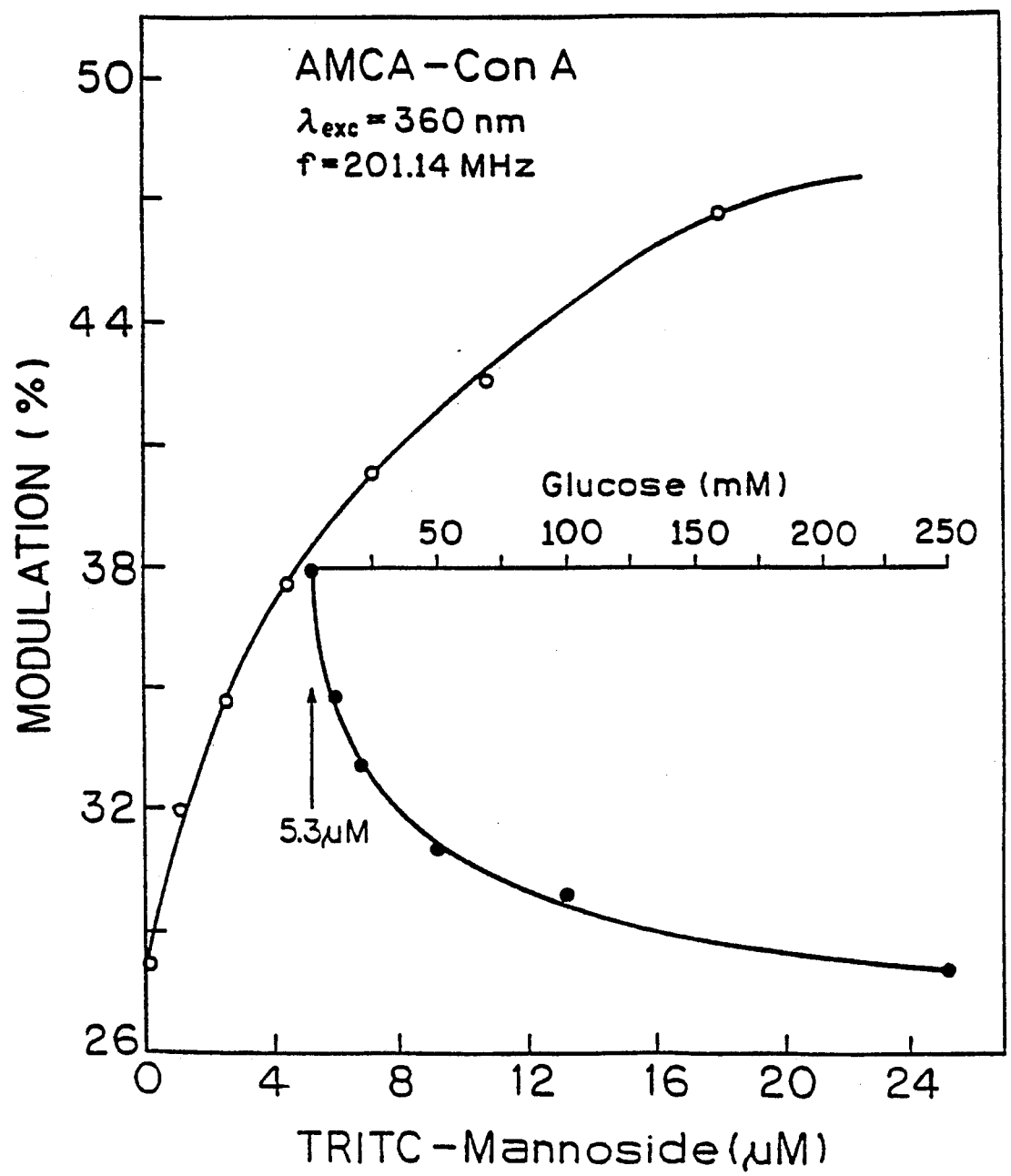
FIG. 21 is a graphical representation of the modulation factor versus the concentration of the acceptor TRITC labelled mannoside for the donor AMCA labelled ConA; the insert in the figure shows the effect of added glucose.

This study was directed to the donor AMCA-ConA and the acceptor TRITC cadaverine mannoside. The relationship between the donor and acceptor emission spectra is shown in FIG. 14. The quenching effect of the acceptor on the fluorescence of the donor is seen in FIG. 15. The displacement of the acceptor by glucose is shown in FIG. 16, with the quenching being increasingly reversed with increasing concentration of the sugar. FIG. 17 shows the decrease in phase angle and increase in modulation upon binding of the acceptor, indicating a decrease in decay time due to energy transfer. As seen in FIG. 18, this effect is reversed by the presence of glucose. FIGS. 19 through 21 represent this reversal of energy transfer in terms of mean lifetime, phase angle and modulation respectively, with the effect of increasing glucose concentration being shown in each case.

The above is for illustrative purposes only. Modifications can be made within the scope of the invention as defined by the appended claims. For example, it is contemplated that the invention is not limited to the measurement of energy transfer and lifetime changes in the manner described above. The energy transfer and the lifetime changes may also be measured via polarization, decreased susceptability to quenching, or the like. It is also contemplated that longer wavelength probes may be used as donors and acceptors, thereby allowing the use of less expensive light sources like modulated HeNe lasers or laser diodes. Similarly, other carriers such as lectins, ricin and wheat germ agglutin may be utilized, permitting detection of other saccharides, conjugated saccharides and polysaccharides.

We claim:

1. A method of optically sensing a saccharide, conjugated saccharide or polysaccharide of interest, said method comprising the steps of:
   exposing an energy transfer donor-acceptor pair to a sample to be analyzed one of the donor-acceptor pair being bound to a carrier, the acceptor of the donor-acceptor pair being capable of competitive displacement with the saccharide, conjugated saccharide or polysaccharide of interest, and at least the donor of the donor-acceptor pair being photoluminescent;
   exciting the sample with radiation;
   detecting the resulting emission beam; and
   calculating the apparent luminescence lifetime of the donor and correlating the apparent luminescent lifetime to the presence of the saccharide, conjugated saccharide or polysaccharide to determine the presence of the saccharide, conjugated saccharide or polysaccharide of interest in the sample.

2. The method of claim 1, wherein the donor is fluorescent.

3. The method of claim 1, wherein the lifetime is calculated using phase-modulation fluorometry.

4. The method of claim 1, wherein the lifetime is calculated using time-resolved fluorometry.

5. The method of claim 1, wherein the sample is excited with a HeNe laser or laser diode.

6. The method of claim 1, wherein the saccharide, conjugated saccharide or polysaccharide of interest is glucose.

7. The method of claim 6, wherein the glucose concentration of the sample is calculated from the apparent luminescence lifetime.

8. The method of claim 6, wherein the donor is selected from the group consisting of Cascade Blue, Texas Red, fluorescein, and 7-amino-4-methylcoumarin-3-carboxylic acid, lanthanides and metal-ligand complexes.

9. The method of claim 6, wherein the acceptor is selected from the group consisting of malachite green-dextran, eosin cadaverine-alpha,D-mannose pyranosyl phenyl and TRITC cadaverine-alpha,D-mannose pyranosyl phenyl.

10. The method of claim 6, wherein the acceptor is bound to a sugar or polymeric sugar carrier.

11. The method of claim 6, wherein the sample is excited with a HeNe laser or laser diode.

12. The method of claim 6, wherein the donor of the donor-acceptor pair is bound to a carrier, and the acceptor of the donor-acceptor pair and any glucose present in the sample compete for binding sites on the carrier.

13. The method of claim 12, wherein the donor is bound to the carrier Concanavalin A.

14. The method of claim 13, wherein the acceptor is bound to a sugar or polymeric sugar carrier.

15. The method of claim 12, wherein the sample is excited with a HeNe laser or laser diode.

* * * * *